(12) United States Patent
Edwards (10) Patent No.: US 11,065,012 B2
(45) Date of Patent: Jul. 20, 2021

(54) DEBRIDER WITH DECLOGGING FEATURE

(71) Applicant: GYRUS ACMI, INC., Southborough, MA (US)

(72) Inventor: Kevin C. Edwards, Olive Branch, MS (US)

(73) Assignee: Gyrus Acmi, Inc., Westborough, MA (US)

(*) Notice: Subject to any disclaimer, the term of this patent is extended or adjusted under 35 U.S.C. 154(b) by 310 days.

(21) Appl. No.: 15/874,065

(22) Filed: Jan. 18, 2018

(65) Prior Publication Data
US 2019/0216473 A1 Jul. 18, 2019

(51) Int. Cl.
*A61B 17/32* (2006.01)
*A61B 17/16* (2006.01)
*A61B 17/3205* (2006.01)

(52) U.S. Cl.
CPC .......... *A61B 17/1659* (2013.01); *A61B 17/16* (2013.01); *A61B 17/32002* (2013.01); *A61B 17/3205* (2013.01); *A61B 2017/1602* (2013.01); *A61B 2017/32004* (2013.01); *A61B 2017/320008* (2013.01); *A61B 2017/32008* (2013.01); *A61B 2017/320028* (2013.01); *A61B 2217/005* (2013.01); *A61B 2217/007* (2013.01)

(58) Field of Classification Search
CPC .... A61B 2017/32008; A61B 17/32002; A61B 17/1659
See application file for complete search history.

(56) References Cited

U.S. PATENT DOCUMENTS

| | | | |
|---|---|---|---|
| 6,293,957 B1 | 9/2001 | Peters et al. | |
| 7,226,459 B2 | 6/2007 | Cesarini et al. | |
| 7,510,563 B2 | 3/2009 | Cesarini et al. | |
| 7,666,200 B2 | 2/2010 | Heisler | |
| 2009/0030437 A1* | 1/2009 | Houser | A61B 18/1442 606/169 |

* cited by examiner

*Primary Examiner* — Olivia C Chang
(74) *Attorney, Agent, or Firm* — Schwegman Lundberg & Woessner, P.A

(57) ABSTRACT

A debrider that includes an outer tubular member, and an inner tubular member located inside the outer tubular member. The inner tubular member includes an aspiration channel. The outer tubular member includes a declogging feature. The declogging feature extends from an inside distal wall of the outer tubular member in a proximal direction towards a distal wall of the inner member. The declogging feature is at least partially received into the aspiration channel through a distal opening defined in the distal end of the inner member, and is configured to push any matter located inside the aspiration channel in a proximal direction.

19 Claims, 5 Drawing Sheets

DEBRIDER WITH DECLOGGING FEATURE

FIELD

These teachings relate to a medical device, and more particularly to a debrider having one or more declogging features.

BACKGROUND

A debrider is a medical device that includes a rotatable and/or reciprocating inner member located within a stationary outer member. The outer member includes a cutting window that is configured to expose a cutting portion of the inner member. During a medical procedure, the cutting portion may be used to shave, cut, resect, abrade, or otherwise remove portions of tissue, bone, or other anatomical features or objects at a surgical site.

The shaved, cut, resected, abraded, or removed portions of the tissue, bone, or other anatomical features or objects may be aspirated away from the surgical site through an aspiration channel defined inside the debrider. At times, however, the shaved, cut, resected, abraded, or removed portions of the tissue, bone, or the other anatomical features may build up inside the aspiration channel and then clog the aspiration channel. A clog in the aspiration channel may interfere with or inhibit the cutting portion of the debrider from properly shaving, cutting, resecting, abrading, or removing additional portions of the tissue, bone, or other anatomical features. Moreover, a clog in the aspiration channel may inhibit or prevent removal of additional shaved, cut, resected, abraded, or removed portions of the tissue, bone, or the other anatomical features from the surgical site, which may contaminate the surgical site and/or make it difficult for the clinician performing the medical procedure to see the surgical site.

One method of declogging or dislodging matter inside of the aspiration channel is to obtain a wire or stylet, insert the wire or stylet into the debrider, and manually push the clogged matter further into the aspiration channel with the wire or stylet. As can be imagined, this may undesirably prolong a medical procedure and/or frustrate the clinician performing the medical procedure. Moreover, inserting and pushing a wire or stylet into the debrider may damage the device.

It may therefore be desirable to have a debrider that can quickly, easily, and automatically dislodge or de-clog buildup of matter as it occurs, or shortly thereafter.

Some examples of debriders are disclosed in U.S. Pat. Nos. 6,293,957, 7,226,459, 7,510,563, and 7,666,200.

SUMMARY

These teachings provide a debrider. The debrider includes an inner member located within an outer member. The inner member is configured to rotate and/or reciprocate within the outer member. The inner member comprises an aspiration channel. The outer member includes a declogging feature. During the reciprocating motion or movement of the inner member, the declogging feature is configured to extend a least partially into the aspiration channel and thus force, push, dislodge, or de-clog any material or matter that may be built up, clogged, accumulated, and/or is present inside the aspiration channel. More specifically, as the inner member reciprocates in a distal direction relative to the stationary outer member, the one or more declogging members that extend in a proximal direction from the outer member are received into the aspiration channel of the inner member and thus force, push, dislodge, or de-clog any material or matter that may be located, built up, clogged, and/or present inside the aspiration channel in a proximal direction as the inner member moves distally. In other words, the debrider according to these teachings utilizes the natural reciprocating motion or movement of the inner member to automatically dislodge clogs or built-up matter inside the aspiration channel as they occur, or shortly thereafter. Accordingly, interruptions during a medical procedure to manually de-clog buildup inside the aspiration channel can be reduced or even eliminated.

These teachings provide a debrider that includes an outer member, and an inner member located inside of the outer member. The outer member includes a declogging feature that is configured to be at least partially received into the aspiration channel.

These teachings provide a debrider that includes an outer tubular member, and an inner tubular member located inside the outer tubular member. The inner tubular member includes an aspiration channel. The outer tubular member includes a declogging feature. The declogging feature extends from an inside distal wall of the outer tubular member in a proximal direction towards a distal wall of the inner member. The declogging feature is at least partially received into the aspiration channel through a distal opening defined in the distal end of the inner tubular member, and is configured to push any matter located inside the aspiration channel in a proximal direction.

These teachings provide a method of using the debrider according to any of the teachings herein. The debrider can be inserted into a surgical site, such as a body cavity. The debrider can be turned on before or after the debrider is inserted into the body cavity. The debrider can be used to shave, cut, resect, abrade, or remove portions of tissue, bone, or the other anatomical features from the body cavity. The debrider can be removed from inside the body cavity. By way of the reciprocating movement of the inner member relative to the outer member, and more specifically during the distal movement of the inner member relative to the outer member, the one or more declogging feature are provided into the aspiration channel of the inner member to move, push, de-clog, and/or force any accumulated matter inside the aspiration channel in a proximal direction to prevent clogs and/or buildup of the matter.

DETAILED DESCRIPTION

These teachings provide a medical device. The medical device may be a shaver, a debrider, or a microdebrider. The medical device may function to shave, cut, resect, abrade, or otherwise remove portions of tissue, bone, or other anatomical features and/or objects at or from a surgical site. For example, the medical device may be used in joint surgery, plastic surgery, various otolaryngologic procedures, including, but not limited to, sinus surgery and tonsillectomy, or a combination thereof.

The medical system may comprise one or more energy sources. The energy source may function to power the medical device, power the suction source, or both. The energy source may function to cause the inner member to reciprocate, rotate, and/or oscillate. For example, the energy source may function to cause the inner tubular member to rotate relative to the outer member, the hand piece, or both in a clockwise direction, a counter clockwise direction, or both. The energy source may function to cause the inner member to move or reciprocate between a proximal position and a distal position relative to the outer member, the hand piece, or both. The energy source may also function to cause the inner member to move or reciprocate into an intermediate position defined between a proximal position and a distal position relative to the outer member, the hand piece, or both. The energy source may function to cause the suction source to generate suction or draw vacuum to move, draw, or suck matter located inside the outer member, the inner member, the aspiration channel, or a combination thereof.

The energy source may be an AC energy source, a DC energy source, or both. The energy source may be a discrete energy source that is located away from the medical device and/or the suction source, and connected thereto, or therewith, with one or more electrical conductors or cords. Additionally, or alternatively, the energy source may be contained within, or may be part of, the medical device. For example, the energy source may be contained within the hand piece. Additionally, or alternatively, the energy source may be contained within, or may be part of the suction source.

The medical system may comprise one or more suction sources. The suction source may function to pull, suck, draw, aspirate or otherwise move or remove shaved, cut, resected, abraded, or removed tissue, bone, or the other anatomical features, objects, and/or fluid, also referred to herein collectively as "matter", from within the outer member, the inner member, the aspiration channel, the medical device, the cutting window, the cutting portion, or a combination thereof. The matter may be moved into a receptacle that is located at a proximal end of the medical device, inside the hand piece, or at a location away from the medical device, for example into the suction source. The suction source may perform the aforementioned functions by generating and applying vacuum, suction, negative pressure to the medical device, the aspiration channel, or both. The suction source may be fluidly connected to the medical device and the one or more aspiration channels via one or more tubes or hoses.

The suction source may be part of the medical device. For example, the suction source may be contained within the hand piece. The suction source may be a discrete component that is separate from the medical device, and connected thereto via one or more tubes or wires.

The suction source may be powered by the energy source that powers the medical device, or may be powered by its own discrete energy source.

The suction source may be turned ON and OFF by manipulating one or more of the user controls. The suction source may turn ON automatically when the medical device is powered (i.e., when the inner member is rotating and/or reciprocating), and the suction source may be turned OFF automatically when the medical device is not powered (i.e., when the inner member is not rotating and/or reciprocating). The suction source may be independently turned ON and OFF while the inner member is or is not rotating and/or reciprocating.

The medical system may comprise an irrigation source. The irrigation source may function to provide irrigation fluid to or through the tubular assembly, the medical device, the aspiration channel, or both. The irrigation fluid may function to assist in the removal of matter from within the aspiration channel. The irrigation fluid may be gravity fed or pressurized to, though, and away from the medical device and/or the aspiration channel. For example, the irrigation fluid may be provided into an annular space or gap defined between the inner and outer member and directed towards a distal end of the medical device. The irrigation fluid may then be drawn or aspirated into the aspiration channel via gravity and/or the suction source, and then moved in a proximal direction inside the aspiration channel by the suction source. The flow of irrigation fluid in a proximal direction inside the aspiration channel may function to move matter located inside the aspiration channel in a proximal direction.

The medical device comprises a hand piece. The hand piece may function to be held by a user. The hand piece may comprise a motor that may be configured to cause the inner member to rotate within and/or relative to a stationary outer member, hand piece or both. The motor may be configured to reciprocate the inner member within and/or relative to the outer member, the hand piece, or both.

The hand piece may contain the energy source for operating the medical device, the medical system, or both. The hand piece may contain the suction source. The hand piece may contain a container or reservoir for collecting the matter that is pulled, sucked, drawn, aspirated or otherwise moved out of or away from the aspiration channel, the cutting portion or window, or surgical site via the suction source.

The medical system, the medical device, the hand piece, or a combination thereof may comprise one or more user controls. The one or more user controls may function to operate the medical system and/or the medical device. Manipulation of the one or more user controls may function to start and stop the medical device, the suction source, or both. Manipulation of the one or more user controls may function to change (i.e., increase or decrease) a rotational speed and/or reciprocating speed of the inner member. Manipulation of the one or more user controls may function to change a rotational direction (clockwise or counterclockwise) of the inner member. Manipulation of the medical device may function to rotate the outer member clockwise or counterclockwise relative to the inner member, the hand piece, the site of interest, or a combination thereof.

Starting the medical device may mean causing the motor to rotate and/or reciprocate the inner member. Starting the suction source may mean causing the suction source to pull, suck, draw, aspirate or move air; cut, resected, sheared, or shaved matter; fluid; or a combination thereof through the aspiration channel towards a proximal end of the tubular assembly. Stopping the medical device may mean causing the inner member to stop or cease rotating and/or reciprocating. Stopping the suction source may mean causing the suction source to stop or cease pulling, sucking, drawing, aspirating, or otherwise moving air; cut, resected, sheared, or shaved matter; fluid; or a combination thereof through the inner channel towards a proximal end of the tubular assembly.

The one or more user controls may include one or more triggers, wheels, levers, buttons, knobs, the like, or a combination thereof. A user control may also include a foot pedal. The user controls may be located on the hand piece, on the tubular assembly, on the suction source, on the energy source, at a remote location (i.e., a foot pedal, for example), or a combination thereof.

The medical device, the tubular assembly, or both comprises one or more outer members. The outer member may function to house, contain, and protect the inner member, the cutting portion of the inner member, or both.

The outer member may be an elongated member that extends along a longitudinal axis. A proximal end of the outer member may be connected to the hand piece. A distal end of the outer member may comprise one or more cutting windows. The outer member may be the portion of the medical device that is inserted into the anatomy or surgical site during a medical procedure.

The outer member may be at least partially hollow, and may define therein an inner portion or channel. The hollow or inner portion of the outer member may be sufficiently sized so that one or more inner members can be received therein and/or moved therein.

The outer member may be stationary. Stationary means that the outer member does not move, rotate, or reciprocate, relative to the hand piece, the inner member, the site of interest, or a combination thereof. However, in some configurations, the outer member may be rotated about its center or longitudinal axis relative to the inner member, the hand piece, the site of interest, or a combination thereof. Rotating the outer member allows a rotational position of the outer window to change, thus exposing the cutting portion of the inner member at various rotational positions. This may allow a clinician to cut, shave, resect, debride and/or remove portions of an object or anatomical feature at various locations, without requiring the clinician to reorient the medical device and/or change their handling or approach with the medical device relative to the object or anatomical feature.

The outer member may be substantially straight or include substantially straight or linear portions; may include one or more angles, bends or arcs; or a combination thereof. The outer member may be entire substantially rigid, substantially flexible, or substantially resilient. The outer member may include portions that are substantially rigid, substantially flexible, substantially resilient, or a combination thereof.

The outer member may comprise one or more cutting windows. The cutting may function to provide access to the inner member, the cutting portion of the inner member, the cutting opening of the inner member, or a combination thereof.

When the cutting opening or cutting portion of the inner member is axially and/or rotationally aligned with the cutting window of the outer member, objects and/or anatomical features can be shaved, cut, resected, and/or abraded. When the cutting opening or cutting portion of the inner member is not axial and/or rotationally aligned with the cutting window of the outer member, objects and/or anatomical features are not shaved, cut, resected, and/or abraded.

The cutting window of the outer member may be a notch, groove, cutout, opening, or absence of material defined or existing in a portion of the circumference of an outer surface of the outer member. The cutting window may have edges at the perimeter of the cutting window defining the cutting window, which may be sharp or serrated to assist in shaving, cutting, resecting, abrading, or otherwise removing tissue, bone, or other anatomical features or objects at the surgical site. The cutting window of the outer member is in communication with the inner member, the cutting opening or cutting portion of the inner member, the aspiration channel, or a combination thereof. The cutting window of the outer member may be in communication with the distal opening(s) defined in the inner member or cutting portion.

The medical device, the tubular assembly, or both comprise one or more inner members. The inner member may be supported, provided, or contained inside the outer member. The inner member may rotate in a planar relationship if the outer member is rotated while the inner member is reciprocating, or the inner and outer members may be independently rotatable.

The inner member may be at least partially hollow and may define therein one or more aspiration channels. The inner member may be substantially straight or include substantially straight or linear portions; may include one or more angles, bends or arcs; or a combination thereof. The inner member may be entire substantially rigid, substantially flexible, or substantially resilient. The inner member may include portions that are substantially rigid, substantially flexible, substantially resilient, or a combination thereof.

The inner member may be rotated within the outer member, while the outer member does not rotate. The inner member may be rotated in a clockwise direction, a counterclockwise direction, or both. The inner member may be oscillated. The inner member may be rotated or oscillated about or around its center longitudinal axis, which may or may not be the same as the center or longitudinal axis of the aspiration channel, outer member, or both. The inner member may be rotated or oscillated by manipulating one or more of the user controls. The inner member may be rotated while stationary (i.e., not-reciprocating), or the inner member may be rotated while reciprocating.

The inner member may be reciprocated within the outer member, while the outer member does not reciprocate. The inner member may be reciprocated or axially moved along its center longitudinal axis, which may or may not be the same as the center or longitudinal axis of the aspiration channel, outer member, or both. The inner member may be reciprocated by manipulating one or more of the user controls. The inner member may be reciprocated while stationary (i.e., not-rotating), or the inner member may be reciprocated while rotating.

In some configurations, the inner member may be reciprocated between a proximal position and a distal position. The proximal position may be defined as a position of the inner member where the inner member is moved towards or closer the hand piece, and the distal position may be defined as a position of the inner member where the inner member is moved away from or farther the hand piece. The proximal position may be defined as a position of the inner member where the cutting portion or cutting window of the inner member is at least partially not-aligned with or exposed through the cutting window of the outer member, and the distal position may be defined as a position of the inner member where the cutting portion or cutting window of the inner member is at least partially aligned with or exposed through the cutting window of the outer member. In the proximal position, an object, tissue, or anatomical feature may be not be shaved, cut, resected, abraded, or otherwise removed with the cutting portion of the inner member. In the distal position, an object, tissue, or anatomical feature may be shaved, but, resected, abraded, or otherwise removed with the cutting portion of the inner member. Moving the inner member from the proximal position into the distal position may cause the one or more declogging features to be received into the aspiration channel to move any matter located or stuck therein in a proximal direction while the inner member is being moved in a distal direction into the distal position.

Figure 12A:
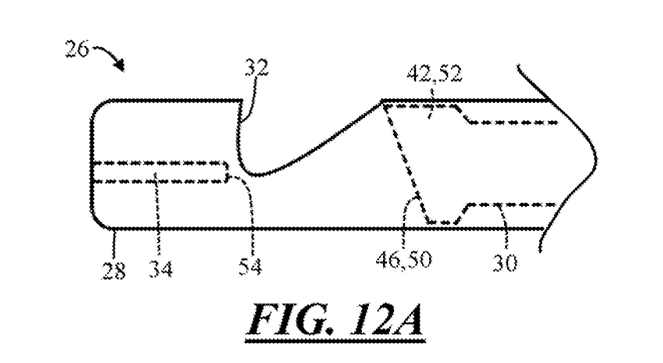
FIG. 12A is a side view of a distal end of the medical device according to these teachings.
Figure 12B:
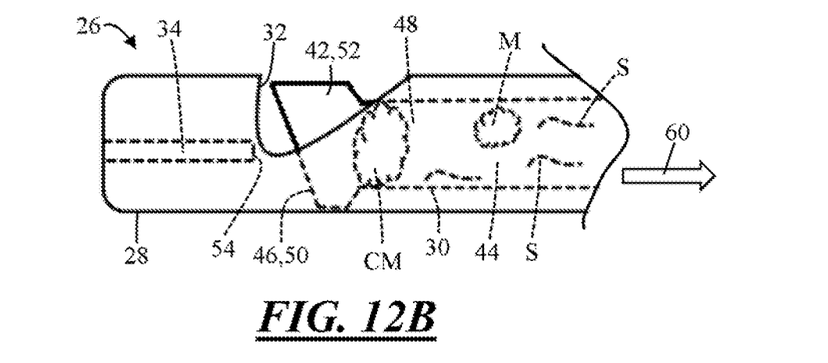
FIG. 12B is a side view of a distal end of the medical device according to these teachings.
Figure 12C:
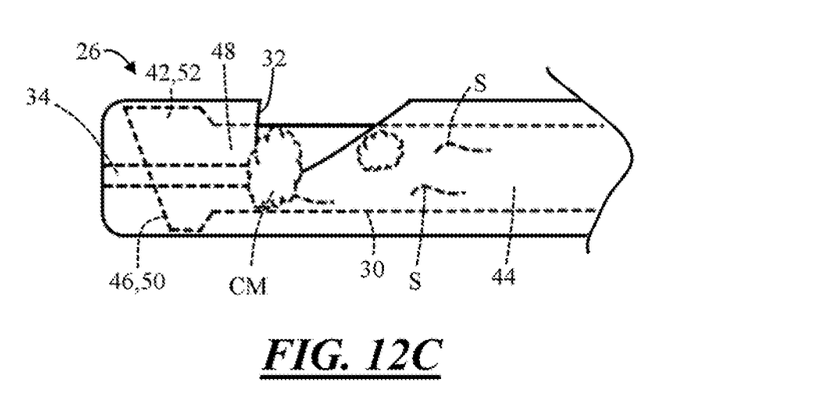
FIG. 12C is a side view of a distal end of the medical device according to these teachings.

In some configurations, the inner member may be reciprocated between a proximal position, a distal position, and an intermediate position therebetween (e.g., FIGS. 12A-12C). The proximal position may be defined as a position of the inner member where the inner member is moved towards or closer the hand piece, and the distal position may be defined as a position of the inner member where the inner member is moved away from or farther from the hand piece. The intermediate position may be a position between the proximal position and the distal position In configurations having the intermediate position, the proximal position may be defined as a position of the inner member where the cutting portion or cutting window of the inner member is located proximal of the cutting window defined in the outer member, and therefore at least partially not-aligned with, or at least partially not-exposed through, the cutting window of the outer member.

The intermediate position may be a position of the inner member where the cutting portion or cutting window of the inner member is exposed through the cutting window in the outer tube and/or at least partially aligned with and at least partially exposed through the cutting window of the outer member so that tissue or objects can be shaved, cut, abraded, resected or a combination thereof with the cutting portion of the inner member. In the intermediate position, the one or more declogging features may, or may not be, received into the aspiration channel. In the intermediate position, the one or more declogging features may, or may not, pass through the cutting opening defined in the cutting portion of the inner member. By not having the one or more declogging features pass through the cutting opening in the cutting portion of the inner member when the inner member is in the intermediate position, the one or more declogging features do not block or prevent the cut, shaved, abraded, or resected objects or anatomical features from falling into or being aspirated into the aspiration channel, as may be the case if a declogging feature were to through the cutting window during the cutting, resecting, abrading, shaving, or otherwise removing portions of the anatomical feature and or object during a procedure.

The distal position may be defined as a position of the inner member that is distal of both the proximal and intermediate positions. The distal position may be defined as a position of the inner member where the cutting portion or cutting window of the inner member is located distal of the cutting window defined in the outer member. In the distal position, the declogging feature may be received into or through the one or more distal openings in the cutting portion of the inner member and into the aspiration channel. Moving the inner member from the intermediate position into the distal position may cause the one or more declogging features to be received into the aspiration channel to move any matter located or stuck therein in a proximal direction while the inner member is being moved in a distal direction into the distal position.

The medical device, the tubular assembly, the inner member, or a combination thereof may comprise one or more cutting portions. The cutting portion may function to shave, cut resect, abrade, or otherwise remove or separate tissue, bone, or the other anatomical features or objects from a surgical site.

The cutting portion may be located at a distal end or at a distal portion of the inner member. The cutting portion may be integrally formed with the inner member. The cutting portion may be mechanically attached to the inner member.

The inner member, the cutting portion, or both may comprise one or more cutting openings. At least a portion of the perimeter of the cutting opening may include one or more teeth, blades, serrations, blades, sharp edges, or features that are adapted contact, engage, and then shave, cut, shear, resect, abrade, or otherwise remove or separate tissue, bone, or the other anatomical features or objects from a surgical site.

The cutting opening is a window, gap, or opening defined in at least a portion of the length of the cutting portion or inner member. The cutting opening functions to perform one or more of the aforementioned functions during rotation and/or reciprocation of the inner member. The cutting opening performs one or more of the aforementioned functions during rotation of the inner member when the cutting portion and/or cutting opening is at least partially aligned with and exposed through the cutting window defined in the outer member.

The cutting opening of the inner member is in communication with the aspiration channel defined within the inner member. Accordingly, pieces of the shaved, cut, resected, abraded, or removed tissue, bone, or the other anatomical features or objects and/or fluid from the surgical site fall into the aspiration channel via the cutting opening via gravity, and/or may be sucked or drawn into the aspiration channel via the cutting opening by way of the suction source. The cutting opening may, or may not, be in communication with the distal opening defined in the distal wall or surface of the inner member or the cutting portion.

The inner member, the cutting portion, or both may comprise one or more distal openings. The one or more distal openings defined in the inner member, the cutting portion, or both may function to provide access to the one or more aspiration channels. The one or more distal openings may function to receive at least a portion of the one or more declogging features so that the one or more declogging features can be received into the one or more aspiration channels so that the declogging features can function to move or push any matter located inside the aspiration channel in a proximal direction. The one or more distal openings may be defined in a distal-most wall of the inner member. The one or more distal openings can be different from the cutting opening.

The inner member, the cutting portion, or both may comprise one or more distal openings, two or more distal openings, three or more distal openings, etc. The number of distal openings may correspond to the number of declogging features. That is, each declogging feature may be received into a specific and independent distal opening. The individual, discrete distal openings may be in communication with a single aspiration channel. However, in some configurations, it may be desirable to have independent and discrete distal openings, corresponding with independent and discrete aspiration channels, corresponding with independent and discrete declogging features.

The size, shape, and orientation of the one or more distal openings may correspond to the size, shape, and orientation of the one or more declogging features. For example, a declogging feature that is angled relative to a longitudinal axis of the aspiration channel may have a distal opening that is similarly angled relative to the longitudinal axis so that the angled declogging feature can be received into the distal opening and into the aspiration channel.

Figure 9:
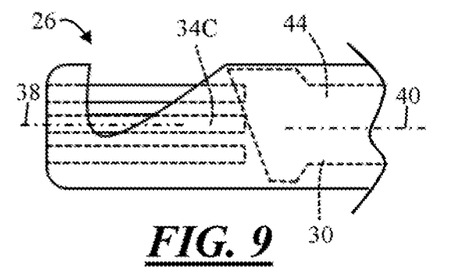
FIG. 9 is a side view of a distal end of the medical device according to these teachings.
Figure 10:
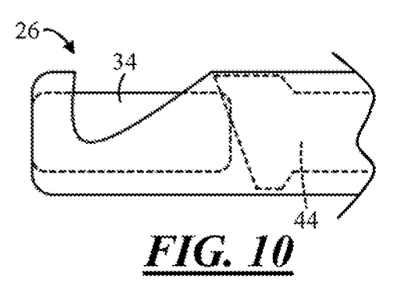
FIG. 10 is a side view of a distal end of the medical device according to these teachings.

Alternatively, the inner member, the cutting portion, or both may comprise one distal opening that is adapted to receive more than one declogging feature (See FIGS. 9, 10, for example).

The inner member may comprise one or more aspiration channels. The one or more aspiration channels may function to provide an area or passageway for the shaved, cut, resected, abraded, or removed tissue, bone, or the other anatomical features to be removed or pulled from the cutting portion of the inner member, from the cutting openings or windows of the inner and outer members, or a combination thereof. Air, irrigation fluid, anatomical fluids, or a combination thereof may also be removed via the one or more aspiration channels.

The one or more aspiration channels may be in fluid communication with the suction source so that that fluids, shaved, cut, resected, abraded, or removed tissue, bone, or the other anatomical features, objects, and/or fluid removed from the surgical site can be drawn, pulled, aspirated, sucked, or otherwise removed from the surgical site, the cutting portion, the cutting opening, the cutting window, or a combination thereof.

However, in some configurations, the one or more aspiration channels may not be in direct fluid communication with the suction source. For example, the one or more aspiration channels may be fluidly disconnected from a suction source and, instead, the shaved, cut, resected, abraded, or removed tissue, bone, or the other anatomical features or objects or fluids from the surgical site can be pushed or moved in a proximal direction of the one or more aspiration channels via the one or more declogging features.

The one or more aspiration channels are preferably in communication with the cutting portion or the cutting window defined in the inner member and the one or more distal openings defined in the distal wall of the cutting portion or inner member.

The one or more aspiration channels may be a channel, bore, passageway, opening, hollow area, or a combination thereof defined in the inner member. The one or more aspiration channels may also be referred to as an inner channel.

The inner member, the one or more aspiration channels, or both may comprise one or more clogging areas. A clogging area may be one or more areas or sections defined inside the aspiration channel of the inner member where shaved, cut, resected, abraded, or removed tissue, bone, or the other anatomical features, objects, and/or fluid from the surgical site are trapped, clogged, stored, built-up, have accumulated, and/or are unable to be moved, drawn, pushed, sucked, or otherwise moved (also referred to as "clogged matter" herein).

A build-up or clog of matter inside the aspiration channel at a clogging area may undesirably prevent the suction source from drawing, sucking, pulling, or otherwise removing the shaved, cut, resected, abraded, or removed tissue, bone, or the other anatomical features, objects, and/or fluid from the surgical site, the cutting portion, the cutting opening, the cutting window, or a combination thereof. A clog may interfere with, or inhibit the cutting portion of the debrider from properly shaving, cutting, resecting abrading, or removing additional portions of the tissue, bone, or other anatomical features. Moreover, a clog in the aspiration channel may inhibit or prevent removal of additional shaved, cut, resected, abraded, or removed portions of the tissue, bone, or the other anatomical features from the surgical site, which may contaminate the surgical site, and/or make it difficult for the clinician performing the medical procedure to see the surgical site.

One or more clogging areas may be located in a narrowing or tapered area of the aspiration channel. One or more clogging areas may be located in an area of the aspiration channel where a substantial amount of the shaved, cut, resected, abraded, or removed tissue, bone, or the other anatomical features, objects, and/or fluid from the surgical site initially accumulates during a medical procedure. For example, one or more clogging areas may be located in or at the cutting opening of the cutting portion, or immediately proximal of the cutting opening of the cutting portion.

The medical device, the outer member, or both may comprise one or more declogging features. The declogging feature may be any feature that functions to push, unclog, dislodge, displace, expel, eject, unblock, clean, spear, harpoon, or otherwise move matter, clogged matter, or both from the one or more aspiration channels, clogged areas or both. The one or more declogging features may function to break up, or break apart, large pieces of the matter, clogged matter, or both located inside or within the one or more aspiration channels or clogged areas. The matter or clogged matter is the shaved, cut, resected, abraded, or removed tissue, bone, or the other anatomical features, objects, and/or fluid from the surgical site.

The declogging features may perform one or more of the aforementioned functions when the inner member is reciprocated. That is, the natural reciprocating motion or movement of the inner member relative to the stationary outer member in the distal direction functions to provide for the one or more declogging features to perform one or more of the aforementioned de-clogging functions. More specifically, when the inner member is moved or reciprocated in a distal direction towards a distal end of the stationary outer member, the one or more declogging features are received into the one or more aspiration channels and thus move or de-clog any matter therein. The matter is moved or pushed further into the aspiration channel in a proximal direction, out of a clogging area, and closer to the suction source, where the matter can be drawn further in a proximal direction and out of the aspiration channel with the suction source. By utilizing the natural reciprocating motion of the inner member to de-clog or move matter inside the aspiration channel, build up or clogs inside the aspiration channel may be reduced or eliminated.

The declogging feature may be a feature located inside the outer member. The declogging feature may extend from a distal wall or distal end of the outer member, and extend in a direction of the inner member, the aspiration channel, or both. The declogging feature may be a feature that extends from or cantilevers from a distal end or a distal surface or a distal wall of the outer member.

The declogging feature may be an elongated member. The declogging feature may be a pin, peg, post, stud, spike, or nub. A cross section of the declogging feature may be substantially round, square, oval, triangular, or have a polygon shape. The declogging feature may have a generally constant or consistent cross section that extends between a proximal end to the distal end where the declogging feature attaches to the distal end wall of the outer member.

The declogging feature may be generally straight or linear. The declogging feature may be flared or drafted along its length to provide for the declogging feature to be easily inserted or received into the distal opening of the inner member, the aspiration channel, or both.

The proximal end of the declogging feature (i.e., the end that is located opposite the distal wall of the outer member from which the declogging feature extends) may be blunt to push the tissue or matter in a proximal direction when the inner member is moved into a distal direction, or the end may be pointed or angled to assist in penetrating or poking the matter or clogged matter to help move the matter or clogged matter in a proximal direction when the inner member is moved in a distal direction.

The declogging feature may be generally rigid, which means that the declogging feature may resist flexing, bending, deformation, and/or deflection. The declogging feature may be at least partially flexible or bendable, which means that the declogging feature may at least partially move, flex, bend, and/or deflect. This may be advantageous to prevent damaging the medical device, the inner member, the outer member, the declogging feature, or a combination thereof if a heavy or rigid clog is present inside the aspiration channel.

The declogging feature may be made of plastic, rubber, metal, or a combination thereof. The declogging feature may be removably attached to the outer member so that in case the declogging feature breaks during use, a new declogging feature can be attached to the outer member. Alternatively, the declogging feature may be permanently attached to the outer member, which means that the declogging feature cannot be separated from the outer member without damaging the declogging feature, the outer member, the medical device, or a combination thereof.

Figure 1:
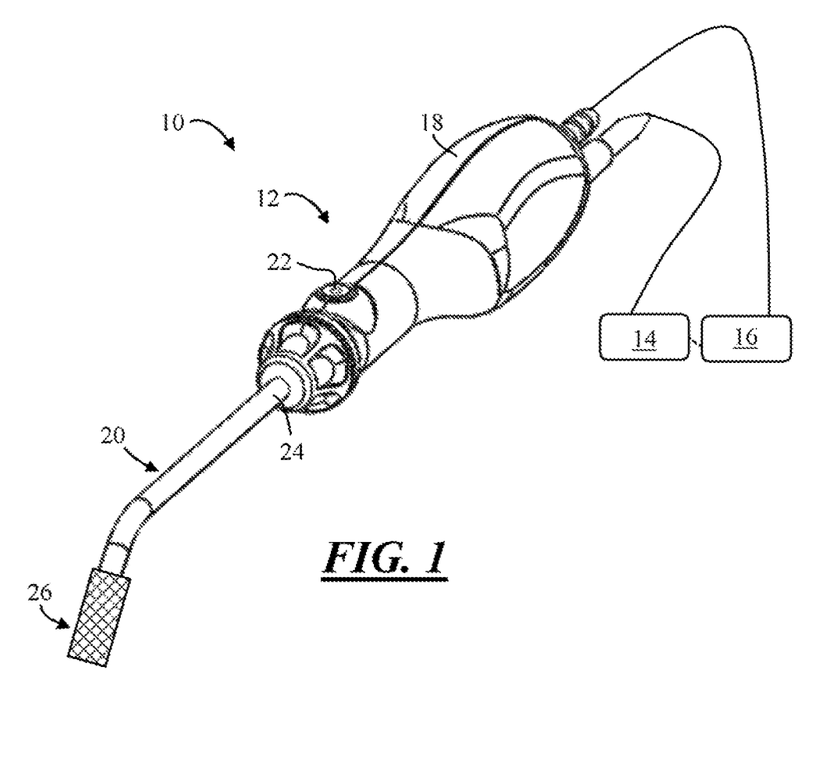
FIG. 1 is perspective view of a medical system comprising a medical device according to these teachings.

FIG. 1 illustrates a medical system 10. The medical system 10 comprises a medical device 12, an energy source 14, and a suction source 16.

The medical device 12 comprises a hand piece 18 and a tubular assembly 20 extending from the hand piece 18. The hand piece 18 comprises one or more user controls 22 for operating the medical system 10, the medical device 12, the suction source 16, or a combination thereof.

The tubular assembly 20 comprises a proximal portion 24 extending from the hand piece 18, and an opposing distal portion 26. While the distal portion 26 is illustrated as being bent or angled relative to the rest of the tubular assembly 20, it is understood that in some configurations the tubular assembly 20 may be a "straight shaft", where the distal portion 26 is generally straight and aligned with the rest of the tubular assembly 20, including the proximal portion 24.

The energy source 14 is configured to power the medical system 10, the medical device 12, the suction source 16, or a combination thereof. The suction source 16 is in fluid communication with the medical device 12, an aspiration channel 44 defined in an inner member 30, or both, and is configured to apply suction through the aspiration channel 44.

Figure 2:
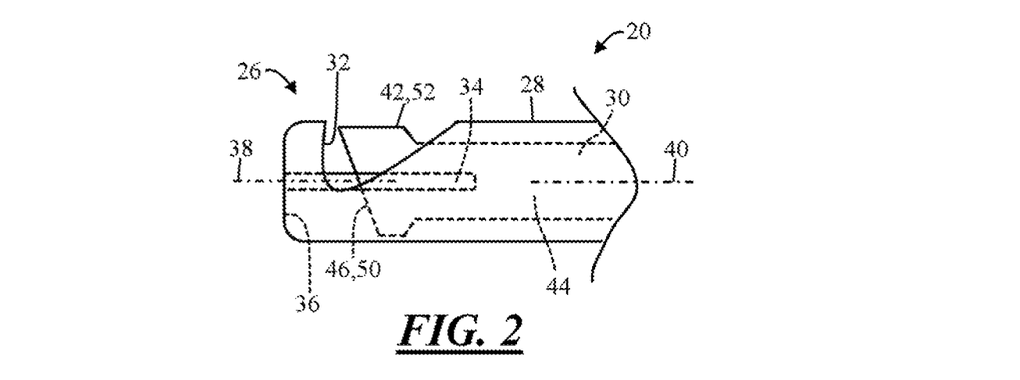
FIG. 2 is a side view of a distal end of a medical device according to these teachings.

FIG. 2 illustrates an exemplary distal portion 26 of the tubular assembly 20. The tubular assembly 20 comprises an outer tubular member 28 and an inner tubular member 30 that is located inside of the outer tubular member 28. The outer member 28 comprises an outer opening or cutting window 32. The outer member 28 comprises a declogging feature 34. The declogging feature 34 extends in a proximal direction from an inside distal wall 36 of the outer member 28 towards the hand piece 18 (FIG. 1). The inner member 30 comprises a cutting portion 42 and an aspiration channel 44. The cutting portion 42 comprises a cutting opening 52 that is in communication with the aspiration channel 44.

The center or longitudinal axis 38 of the declogging feature 34 may be the same as or generally aligned with a center or longitudinal axis 40 of the inner member 30 or aspiration channel 44 defined in the inner member 30. However, as will be discussed further below, the center or longitudinal axis 38 of the declogging feature 34 need not be the same as or aligned with a center or longitudinal axis 40 of the inner member 30 or aspiration channel 44.

The cutting opening 52 of the inner member 30 is in communication with the aspiration channel 44. The inner member 30 also comprises a distal opening 50 defined in a distal wall 46 of the inner member 30 or cutting portion 42. The distal opening 50 is also in communication with the aspiration channel 44, and may be in communication with the cutting opening 52 in the cutting portion 42 as well.

The inner member 30 is in communication with the energy source 14. By manipulating one or more of the user controls 22 on the hand piece 18 or at a remote location, the inner member 30 can be rotated about or around its center or longitudinal axis 40. By manipulating one or more of the user controls 22 on the hand piece 18 or at a remote location, the inner member 30 can move or reciprocate along its center or longitudinal axis 40 between a distal position illustrated in FIG. 2 and a proximal position illustrated in both FIGS. 3 and 4. By manipulating one or more of the user controls 22 on the hand piece 18 or at a remote location, the inner member 30 can be rotated about or around its center or longitudinal axis 40, while the inner member 30 is moved between the distal and proximal positions, or while the inner member 30 is stationary and not reciprocating between the distal and proximal positions.

Figure 3:
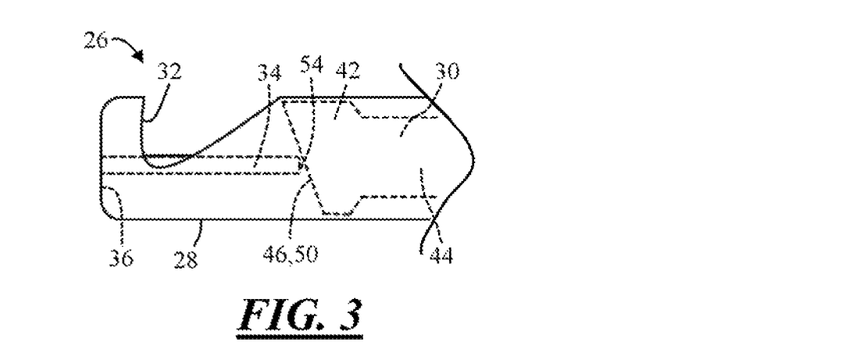
FIG. 3 is a side view of a distal end of a medical device according to these teachings.

FIG. 3 illustrates an example of the inner member 30 in the proximal position. In the proximal position, the inner member 30 is retracted away from the inside distal wall 36 of the outer member 28. In the proximal position, the cutting portion 42 is not aligned with the cutting window 32 defined in the outer member 28. In the proximal position, the declogging feature 34 is not received into the aspiration channel 44 of the inner member 30. In the proximal position, a proximal end 54 of the declogging feature 34 is located forward or distal of the distal opening 50 defined in the distal wall 46 of the inner member 30 or cutting portion 42.

Figure 4:
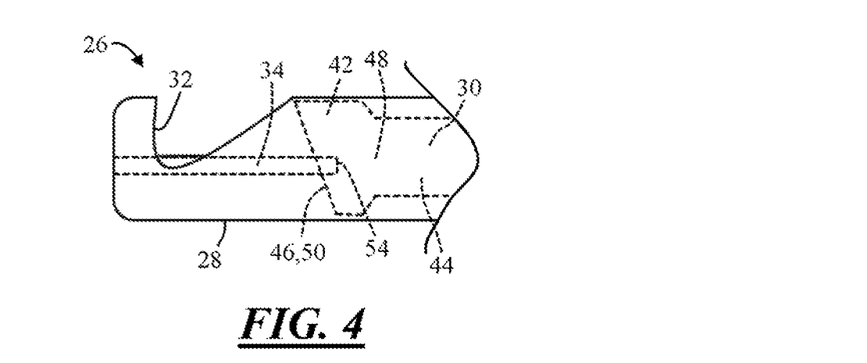
FIG. 4 is a side view of a distal end of a medical device according to these teachings.

FIG. 4 illustrates another example of the inner member 30 in the proximal position. In the proximal position, the proximal end 54 of the declogging feature 34 may be at least partially received into the aspiration channel 44 or into the distal opening 50 defined in the distal wall 46 of the inner member 30 or cutting portion 42; however, the proximal end 54 of the declogging feature 34 is located forward or distal of a clogging area 48 defined inside the aspiration channel 44 and discussed further below. In the proximal position, the cutting portion 42 is not aligned with the cutting window 32 defined in the outer member 28.

Figure 5A:
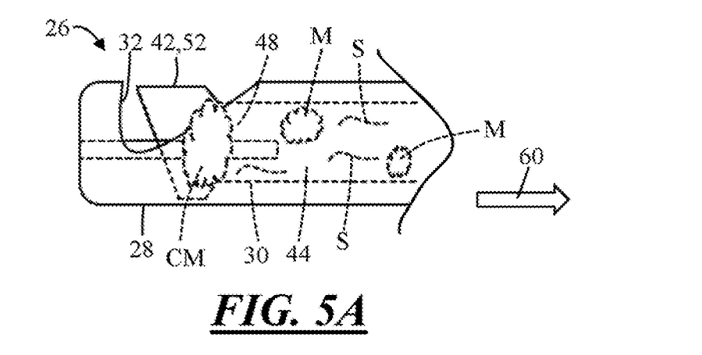
FIG. 5A is a side view of a distal end of the medical device according to these teachings.
Figure 5B:
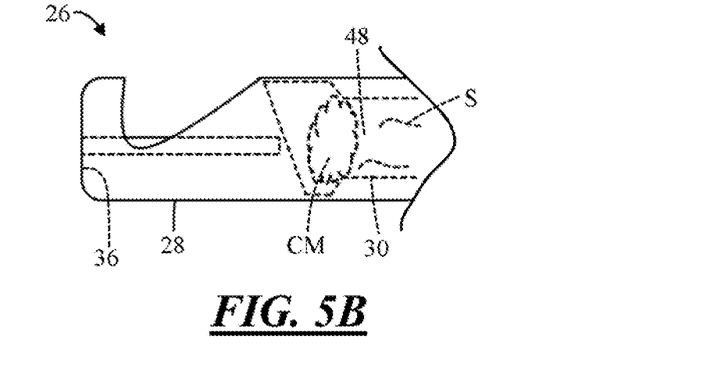
FIG. 5B is a side view of a distal end of the medical device according to these teachings.
Figure 5C:
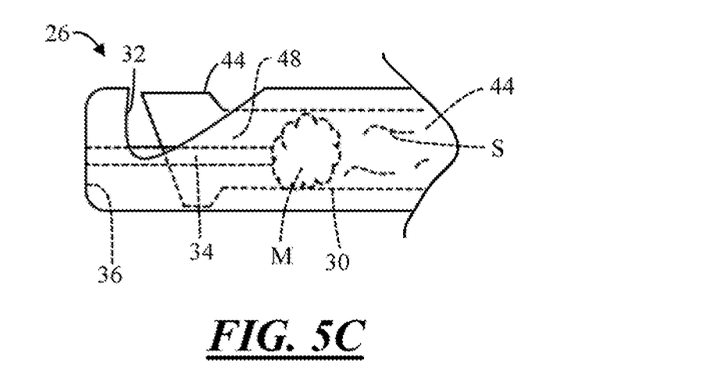
FIG. 5C is a side view of a distal end of the medical device according to these teachings.

FIGS. 5A-5C illustrate the reciprocating movement of the inner member 30 relative to the outer member 28. The declogging feature 34 illustrated in these figures 5A-5C can be replaced with any of the declogging feature(s) illustrated or described herein.

Also, while each of the FIGS. 5A-5C illustrate the inner member 30 in discrete positions, the reciprocating movement of the inner member 30 between these positions may be smooth or continuous or uninterrupted, meaning the inner member 30 does not pause or stop or start and stop in these positions during a medical procedure. Instead, the inner member 30 moves or reciprocates between these positions in a continuous manner. However, in some applications, it may be desirable to have the inner member 30 reciprocate in a start-and-stop manner between one or more of these positions, or to slow, stop, pause, or cease moving at one or more of these positions. Therefore, it is within the scope of this disclosure to have an inner member 30 that is configured to reciprocate in a start-and-stop manner between one or more of these positions, or to slow, stop, pause, or cease moving at one or more of these positions during a medical procedure. While starting and stopping, slowing, pausing, or ceasing movement of the inner member 30, the inner member 30 may continue to rotate, or the inner member 30 may slow, pause, or cease rotating. In FIG. 5A, the inner member 30 is moved into or towards the distal position where the cutting portion 42 is located within or exposed through the cutting window 32 defined in the outer member 28. During a medical procedure, contacting the rotating and reciprocating cutting portion 42 with an object, tissue, bone, or other anatomical features at a surgical site may result in shaving, cutting, resecting, abrading, or otherwise removing portions of the object, tissue, bone, or other anatomical features. Due to gravity and/or the suction S applied by the suction source 16 (FIG. 1) to the aspiration channel 44, the shaved, cut, resected, abraded, or removed object, tissue, bone, or the other anatomical features, hereafter matter M, may fall into or may be aspirated into the aspiration channel 44 of the inner member 30 via the cutting opening 52 defined in the cutting portion 42. The suction S applied by the suction source 16 may aspirate the matter M away from the surgical site, the cutting portion 42, the cutting window 32, or a combination thereof in a proximal direction 60 through the aspiration channel 44.

However, some matter M may build up or get stuck inside the aspiration channel 44, for example at the clogging area 48 inside the aspiration channel 44. This clogged matter CM may comprise pieces of the shaved, cut, resected, abraded, or removed tissue, bone, or the other anatomical features from the surgical site that are too large to fit through the aspiration channel 44; may be a build-up of small pieces of the shaved, cut, resected, abraded, or removed tissue, bone; may comprise fluids or other anatomical features from the surgical site that builds up and gets stuck, jammed, or clogged at the clogging area 48 inside the aspiration channel 44. When clogged matter CM is stuck, jammed, or clogged inside the aspiration channel 44, additional shaved, cut, resected, abraded matter M cannot be aspirated into and through the aspiration channel 44, which may undesirably cause additional shaved, cut, resected, abraded, matter to accumulate at the surgical site or dirty or contaminate the working environment, for example.

In FIG. 5B, the inner member 30 is reciprocated or axially moved towards or into the proximal position where the inner member 30 is moved or retracted away from the inside distal wall 36 of the outer member 28. The clogged material CM remains stuck at the clogging area 48, while the suction source 16 continues to apply suction S to try to move the clogged matter CM out of the clogging area 48.

In FIG. 5C, the inner member 30 is reciprocated or axially moved back towards or into the distal position towards the inside distal wall 36. While moving the inner member 30 towards or into the distal position, the declogging feature 34 is received into the aspiration channel 44, contacts the clogged matter CM, and forces or pushes the clogged matter CM past the clogging area 48 as the inner member 30 is moved further into the distal position. After the clogged matter CM is moved proximal or past the clogging area 48 and/or is broken down into smaller pieces, the clogged matter CM becomes matter M that can be aspired in a proximal direction via the suction S from the suction source 16.

When comparing FIGS. 5B and 5C, it can be seen that the declogging feature 34 contacts and pushes the clogged matter CM (FIG. 5B) before the cutting portion 42 is aligned with or exposed through the cutting window 32 in the outer member 28. This advantageously allows for any clogged matter CM to be removed or freed from the clogging area 48 before the cutting portion 42 is aligned with or exposed through the cutting window 32 and the cutting portion 42 continues to shave, cut, resect, abridge, or otherwise remove additional portions of tissue, bone, or the other anatomical features at a surgical site.

FIGS. 6-11 illustrate various configurations of the distal portion 26 of the tubular assembly 20.

Figure 6:
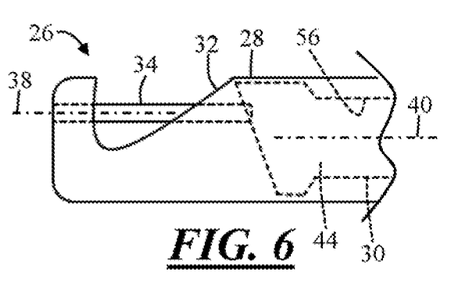
FIG. 6 is a side view of a distal end of the medical device according to these teachings.

In FIG. 6, the center or longitudinal axis 38 of the declogging feature 34 is offset or off-center relative to the center or longitudinal axis 40 of the inner member 30 or aspiration channel 44. The declogging feature 34 is arranged in close proximity to or is even configured to contact or scrape an edge or surface 56 of the aspiration channel 44. This may advantageously prevent matter from sticking to wall or surfaces of the aspiration channel 44. The declogging feature 34 extends or passes through the cutting window 32 defined in the outer member 28.

Figure 7:
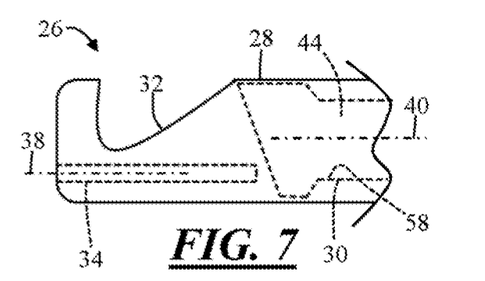
FIG. 7 is a side view of a distal end of the medical device according to these teachings.

In FIG. 7, the center or longitudinal axis 38 of the declogging feature 34 is again offset or off-center relative to the center or longitudinal axis 40 of the inner member 30 or aspiration channel 44. The declogging feature 34 is arranged in close proximity to or is even configured to scrape an edge or surface 58 of the aspiration channel 44. This may advantageously prevent matter from sticking to wall or surfaces of the aspiration channel 44. The declogging feature 34 extends generally below the cutting window 32 defined in the outer member 28.

FIG. 10 illustrates the outer member 28 having two declogging features 34A, 34B. The center or longitudinal axis of both declogging features 34A, 34B is offset or off-center relative to the center or longitudinal axis 40 of the inner member 30 or aspiration channel 44. The declogging feature 34A is arranged in close proximity to or even configured to scrape an edge or surface 56 of the aspiration channel 44, and the declogging feature 34B is arranged in close proximity to or even configured to scrape an opposing edge or surface 58 of the aspiration channel 44. This may advantageously prevent matter from sticking to wall or surfaces of the aspiration channel 44.

Figure 8:
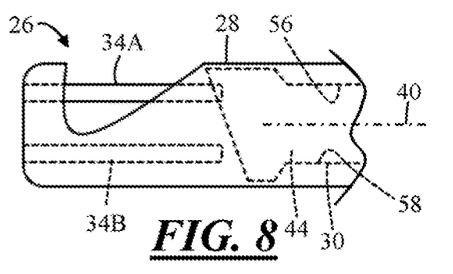
FIG. 8 is a side view of a distal end of the medical device according to these teachings.

FIG. 9 is substantially similar to FIG. 8, but adds a third declogging feature 34C. The center or longitudinal axis 38 of the third declogging feature 34C may be the same as or arranged along the center or longitudinal axis 40 of the inner member 30 or aspiration channel 44. Of course, the center or longitudinal axis 38 of the third declogging feature 34C may also be offset or off-center relative to the center or longitudinal axis 40 of the inner member 30 or aspiration channel 44.

FIG. 10 illustrates the declogging feature 34 having a cross-sectional size that is substantially the same size as and/or substantially matches a cross-sectional shape of the aspiration channel 44.

Figure 11:
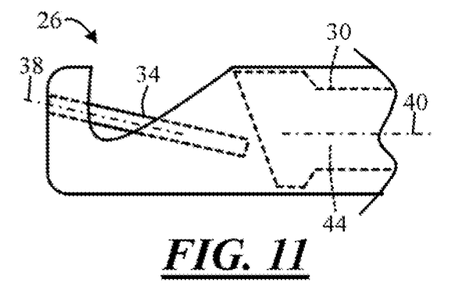
FIG. 11 is a side view of a distal end of the medical device according to these teachings.

FIG. 11 illustrates a declogging feature 34 having a center axis 38 that is angled relative to the longitudinal axis 40 of the aspiration channel 44 or inner member 30.

FIGS. 12A-12C illustrate the reciprocating movement or motion of the inner member 30.

FIG. 12A illustrates the inner member 30 in a proximal position, FIG. 12B illustrates the inner member 30 in an intermediate position, and FIG. 12C illustrates the inner member 30 in a distal position.

The declogging feature 34 illustrated in these FIGS. 12A-12C can be replaced with any of the declogging feature(s) illustrated or described herein.

Also, while each of the FIGS. 12A-12C illustrate the inner member 30 in discrete positions, the reciprocating movement of the inner member 30 between these positions may be smooth or continuous or uninterrupted, meaning the inner member 30 does not pause or stop or start and stop in these positions during a medical procedure. Instead, the inner member 30 moves or reciprocates between these positions in a continuous manner. However, in some applications, it may be desirable to have the inner member 30 reciprocate in a start-and-stop manner between one or more of these positions, or to slow, stop, pause, or cease moving at one or more of these positions. Therefore, it is within the scope of this disclosure to have an inner member 30 that is configured to reciprocate in a start-and-stop manner between one or more of these positions, or to slow, stop, pause, or cease moving at one or more of these positions during a medical procedure. While starting and stopping, slowing, pausing, or ceasing movement of the inner member 30, the inner member 30 may continue to rotate, or the inner member 30 may slow, pause, or cease rotating.

Referring specifically to FIG. 12A, the inner member 30 is in the proximal position. In the proximal position, the cutting portion 42 and cutting opening 52 are proximally located relative to the cutting window 32 defined in the outer member 28. Therefore, the cutting portion 42 is not exposed through the cutting window 32 and the anatomical feature or object is not shaved, cut, resected, abraded, or otherwise removed.

The proximal end 54 of the declogging feature 34 is located distal of the cutting window 32 in the outer member 28 and the cutting portion 42 of the inner member 30.

Referring now to FIG. 12B, the inner member 28 is moved or reciprocated distally into an intermediate position, where the cutting member 42 and cutting opening 52 are at least partially aligned with and at least partially exposed through the cutting window 32 defined in the outer member 32. In the intermediate position, the proximal end 54 of the declogging feature 34 remains distal of the cutting window 32 of the outer member 30, the cutting opening 52 in the cutting portion 42, and the aspiration channel 44.

During the medical procedure with the inner member 28 in the intermediate position, contacting the rotating and/or reciprocating cutting portion 42 with an object, tissue, bone, or other anatomical features at a surgical site results in shaving, cutting, resecting, abrading, or otherwise removing portions of the object, tissue, bone, or other anatomical features. Due to gravity and/or the suction S applied by the suction source 16 (FIG. 1) to the aspiration channel 44, the shaved, cut, resected, abraded, or removed object, tissue, bone, or the other anatomical features, hereafter matter M, may fall into or may be aspirated into the aspiration channel 44 of the inner member 30 via the cutting opening 52 defined in the cutting portion 42. The suction S applied by the suction source 16 may aspirate the matter M away from the surgical site, the cutting portion 42, the cutting window 32, or a combination thereof in a proximal direction 60 through the aspiration channel 44.

By having the declogging feature 34 distal of the cutting window 32 and the cutting opening 52 of the cutting portion 42 when the inner member 28 is in the intermediate position, the declogging feature 34 does not interfere with and/or block or prevent any of the shaved, cut, resected, abraded, or removed object, tissue, bone, or the other anatomical features, hereafter matter M, from falling into and/or being aspirated into the aspiration channel 44 of the inner member 30 via the cutting opening 52 defined in the cutting portion 42.

However, some matter M may build up or get stuck inside the aspiration channel 44, for example, at the clogging area 48 inside the aspiration channel 44. This clogged matter CM may comprise pieces of the shaved, cut, resected, abraded, or removed tissue, bone, or the other anatomical features from the surgical site that are too large to fit through the aspiration channel 44; may be a build-up of small pieces of the shaved, cut, resected, abraded, or removed tissue, bone; may comprise fluids or other anatomical features from the surgical site that builds up and gets stuck, jammed, or clogged at the clogging area 48 inside the aspiration channel 44. When clogged matter CM is stuck, jammed, or clogged inside the aspiration channel 44, additional shaved, cut, resected, abraded matter M cannot be aspirated into and through the aspiration channel 44, which may undesirably cause additional shaved, cut, resected, abraded, matter to accumulate at the surgical site or dirty or contaminate the working environment, for example.

As the inner member 30 is the moved or reciprocated into the distal position illustrated in FIG. 12C, where the cutting portion 42 is moved distal of the cutting window 32 defined in the outer member 28, the declogging feature 34 is received into the aspiration channel 44, contacts the clogged matter CM, and forces or pushes the clogged matter CM past the clogging area 48 as the inner member 30 is continues to be moved further into the distal position. After the clogged matter CM is moved proximal or past the clogging area 48 and/or is broken down into smaller pieces, the clogged matter CM becomes matter M that can be aspired in a proximal direction via the suction S from the suction source 16.

LISTING OF REFERENCE NUMERALS 10 medical system
12 medical device
14 energy source
16 suction source
18 hand piece
20 tubular assembly
22 user control
24 proximal portion of tubular assembly 20
26 distal portion of tubular assembly 20
28 outer member, outer tubular member
30 inner member, inner tubular member
32 cutting window, outer opening of outer member 28
34 declogging feature
36 inside distal wall of outer member 28
38 center or longitudinal axis of declogging feature 34
40 center or longitudinal axis of inner member 30 or aspiration channel 44
42 cutting portion of inner member 30
44 aspiration channel of inner member 30

46 distal wall of the inner member 30 or cutting portions 42
48 clogging area
50 distal opening in distal wall 46 of inner member 30
52 cutting opening in the cutting portion 42
54 proximal end of declogging feature 34
56 edge or surface 56 defining the aspiration channel 44
58 edge or surface 56 defining the aspiration channel 44
60 proximal direction The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A debrider comprising:
an outer member, and
an inner member located inside of the outer member, the inner member comprising an aspiration channel, a distal opening, and a cutting opening through which matter enters the aspiration channel during a medical procedure;
wherein the outer member comprises a declogging feature that is configured to be at least partially received into the aspiration channel; and
wherein the distal opening extends along a first plane relative to a center longitudinal axis of the aspiration channel and the cutting opening extends along a second, different plane relative to the center longitudinal axis of the aspiration channel.

2. The debrider according to claim 1, wherein the declogging feature is an elongated member that extends in a proximal direction from a distal end wall of the outer member.

3. The debrider according to claim 2, wherein the distal opening extends through a distal wall of the inner member, and the declogging feature is configured to be at least partially received into the aspiration channel through the distal opening.

4. The debrider according to claim 3, wherein the inner member is configured to axially move within the outer member between a proximal position and a distal position, the declogging feature is at least partially received into the aspiration channel only when the inner member is in the distal position.

5. The debrider according to claim 3, wherein the inner member is configured to axially move within the outer member between a proximal position and a distal position, the declogging feature is at least partially received into the aspiration channel when the inner member is in both the proximal position and the distal position.

6. The debrider according to claim 2, wherein a center longitudinal axis of the declogging feature is generally aligned with the center longitudinal axis of the aspiration channel.

7. The debrider according to claim 2, wherein a center longitudinal axis of the declogging feature is offset from the center longitudinal axis of the aspiration channel.

8. The debrider according to claim 2, wherein a center longitudinal axis of the declogging feature is angled relative to a center longitudinal axis of the inner member.

9. The debrider according to claim 2, wherein the outer member comprises two or more declogging features extending in the proximal direction from the distal end wall of the outer member, and all of the declogging features are configured to be at least partially received into the aspiration channel.

10. The debrider according to claim 2, wherein a cross section of the declogging feature is generally the same size as a cross section of the aspiration channel.

11. A debrider comprising:
an outer tubular member, and
an inner tubular member located inside the outer tubular member, the inner tubular member comprising an aspiration channel, a distal end, and a distal opening defined in the distal end;
wherein the outer tubular member comprises a declogging feature that extends from an inside distal wall of the outer tubular member in a proximal direction, and which is configured to be at least partially received into the aspiration channel through the distal opening defined in the distal end of the inner member;

wherein the inner tubular member comprises a cutting opening through which matter enters the aspiration channel during a medical procedure, and the declogging feature is configured to push at least some of the matter located inside the aspiration channel in a proximal direction; and wherein the distal opening extends along a first plane relative to a center longitudinal axis of the aspiration channel and the cutting opening extends along a second, different plane relative to the center longitudinal axis of the aspiration channel.

12. The debrider according to claim 11, wherein a center longitudinal axis of the declogging feature is generally aligned with the center longitudinal axis of the aspiration channel.

13. The debrider according to claim 11, wherein a center longitudinal axis of the declogging feature is generally offset from the center longitudinal axis of the aspiration channel.

14. The debrider according to claim 11, wherein a center longitudinal axis of the declogging feature is angled relative to the center longitudinal axis of the aspiration channel.

15. The debrider according to claim 11, wherein a cross section of the declogging feature is substantially the same size as a cross section of the aspiration channel.

16. The debrider according to claim 11, wherein the outer tubular member comprises two declogging features that both extend from the inside distal wall of the outer tubular member, and both of the declogging feature are configured to be at least partially received into the aspiration channel.

17. The debrider according to claim 16, wherein one of the two declogging features is located adjacent a first inside surface of the aspiration channel, and the other of the two declogging features is located adjacent an opposing second inside surface of the aspiration channel.

18. The debrider according to claim 17, wherein the outer tubular member comprises a third elongated declogging feature, and wherein a center longitudinal axis of the third declogging feature is generally aligned with the center longitudinal axis of the aspiration channel.

19. A debrider comprising:

an outer tubular member, and an inner tubular member located inside the outer tubular member, the inner tubular member comprising an aspiration channel, a distal end, and a distal opening defined in the distal end;

wherein the outer tubular member comprises a declogging feature that extends from an inside distal wall of the outer tubular member in a proximal direction, and which is configured to be at least partially received into the aspiration channel through the distal opening in the distal end of the inner member;

wherein the inner tubular member comprises a cutting opening through which matter enters the aspiration channel during a medical procedure, and the declogging feature is configured to push at least some of the matter located inside the aspiration channel in a proximal direction; and wherein the distal opening extends along a first plane that intersects a center longitudinal axis of the aspiration channel and the cutting opening extends along a second plane that is substantially parallel to the center longitudinal axis of the aspiration channel.

* * * * *